US008805528B2

(12) United States Patent
Corndorf

(10) Patent No.: US 8,805,528 B2
(45) Date of Patent: Aug. 12, 2014

(54) CHANNEL ASSESSMENT AND SELECTION FOR WIRELESS COMMUNICATION BETWEEN MEDICAL DEVICES

(75) Inventor: Eric D. Corndorf, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 447 days.

(21) Appl. No.: 12/414,946

(22) Filed: Mar. 31, 2009

(65) Prior Publication Data

US 2010/0249881 A1    Sep. 30, 2010

(51) Int. Cl.
 *A61N 1/39* (2006.01)
(52) U.S. Cl.
 USPC .................. 607/60; 607/32; 455/62
(58) Field of Classification Search
 USPC ............ 607/30–32, 59–60; 128/903
 See application file for complete search history.

(56) References Cited

U.S. PATENT DOCUMENTS

| | | | |
|---|---|---|---|
| 4,197,500 A | 4/1980 | Klein et al. | |
| 7,162,307 B2 | 1/2007 | Patrias | |
| 7,280,872 B1 | 10/2007 | Mosesov et al. | |
| 8,019,429 B2 * | 9/2011 | Aschbacher et al. | 607/56 |
| 2007/0049983 A1 | 3/2007 | Freeberg | |
| 2008/0058900 A1 | 3/2008 | Berthelsdorf et al. | |
| 2008/0253327 A1 * | 10/2008 | Kohvakka et al. | 370/330 |
| 2008/0264431 A1 | 10/2008 | Masoud et al. | |
| 2010/0014572 A1 * | 1/2010 | Nowotarski et al. | 375/228 |
| 2010/0036459 A1 * | 2/2010 | Ramakrishnan et al. | 607/60 |

FOREIGN PATENT DOCUMENTS

| | | |
|---|---|---|
| WO | WO2007114743 | 10/2007 |
| WO | WO2006068862 | 3/2009 |

OTHER PUBLICATIONS (PCT/US2010/028139) PCT Notification of Transmittal of the International Search Report and the Written Opinion of the International Searching Authority.

* cited by examiner

*Primary Examiner* — Catherine Voorhees
(74) *Attorney, Agent, or Firm* — Michael J. Ostrom; Stephen W. Bauer

(57) ABSTRACT

Channel assessment and selection for wireless communication is made between two or more medical devices, such as between an implantable medical device (IMD) and a non-implanted medical device, between two IMDs, or between two non-implanted medical devices. A telemetry module of a medical device operating in accordance with the techniques of this disclosure obtains measured ambient power levels on a plurality of channels of a frequency band regulation, such as the ten channels of the MICS band regulation. The telemetry module computes channel assessment values for at least a portion of the plurality of channels based on the measured ambient power levels on at least one other channel of the plurality of channels and selects a channel to transmit on based on the channel assessment values.

16 Claims, 5 Drawing Sheets

CHANNEL ASSESSMENT AND SELECTION FOR WIRELESS COMMUNICATION BETWEEN MEDICAL DEVICES

TECHNICAL FIELD

The disclosure relates generally to implantable medical devices and, in particular, to channel assessment for selecting a channel for communication between an implantable medical device and another device.

BACKGROUND

A wide variety of implantable medical devices (IMDs) that deliver a therapy to or monitor a physiologic or biological condition of a patient, or both, have been clinically implanted or proposed for clinical implantation in patients. The IMD may deliver therapy to or monitor a physiological or biological condition with respect to a variety of organs, nerves, muscles or tissues of the patients, such as the heart, brain, stomach, spinal cord, pelvic floor, or the like. The therapy provided by the IMD may include electrical stimulation therapy, drug delivery therapy or the like.

The IMD may exchange communications with another device. The IMD may exchange communications with an external medical device, such as a programming device or a monitoring device (e.g., either attached to the patient or otherwise located near the patient). Alternatively, or additionally, the IMD may communicate with another implantable device, e.g., another device that forms part of an intra-body communications network. The information exchanged may be information related to a condition of the patient, such as physiological signals measured by one or more sensors, or information related to a therapy delivered to the patient. This information may be previously stored or real-time information. The IMD may also receive information from the programmer, such as configuration information that may be used to configure a therapy to be provided to the patient.

The IMD and the other device may exchange information using radio frequency (RF) communications. For example, the IMD and the other device may communicate in the 402-405 megahertz (MHz) frequency band in accordance with the Medical Implant Communications Service (MICS) band regulations. As another example, the IMD and the other device may communicate over the 401-402 MHz or 405-406 MHz frequency bands in accordance with the Medical External Data Service (MEDS) band regulations. In either case, the IMD and/or the other device with which the IMD communicates performs channel assessment to identify one of the channels of the particular frequency band to use for exchanging communications.

SUMMARY

This disclosure relates to channel assessment and selection for wireless communication between two or more medical devices, such as between an IMD and a non-implanted medical device, between two IMDs, or between two non-implanted medical devices. A channel selection module, which may be part of a processor or telemetry module of a medical device, operating in accordance with the techniques of this disclosure assesses at least a portion the channels of a frequency band regulation as a function of the ambient power on the respective channels and the ambient power on at least one other channel. Thus, in assessing the channels, the channel selection module not only analyzes the ambient power on the channel being assessed (sometimes referred to as received "on channel" power), but also on the ambient power on other channels, such as channels adjacent to the channel being assessed.

For example, the channel selection module may measure the amount of ambient radio frequency (RF) power on each channel of the frequency band regulation, e.g., the MICS frequency band regulation or the MEDS frequency band regulation. The channel selection module computes a channel assessment value for each of the channels of the frequency band regulation using at least the measured ambient power of at least one other channel of the frequency band regulation. In one example, the channel selection module selects a subset of the channels that have lowest measured ambient powers and computes the channel assessment value for each of the selected subset of channels based on the measured ambient power of an adjacent channel immediately before the channel being assessed and an adjacent channel immediately after the channel being assessed. In other examples, the channel selection module computes the channel assessment values for each of the channels using more channels located further (in frequency) from the channel being assessed. In further examples, the channel selection module may measure ambient power on channels outside of the frequency band regulation to which the channel being assessed belongs, e.g., particularly in assessing channels on or near the edge of the frequency band regulation, and use the measured power on the channel outside of the frequency band regulation in computing the channel assessment value.

The channel selection module of the medical device selects the channel with the channel assessment value indicative of the best estimated telemetry performance. Assessing and selecting the channels of the frequency band regulation as a function of at least one other channel allows the channel selection module of the medical device to better select the channel for use in communicating with other medical devices by accounting for desensitization that may occur due to large RF power usage in adjacent channels. Such a scheme may be particularly useful in an environment in which a number of medical devices are communicating using a limited number of channels, e.g., in a hospital, nursing home, doctor's office, or the like.

In one example, this disclosure is directed to a method comprising obtaining measured ambient power levels on a plurality of channels of a frequency band regulation, computing channel assessment values for at least a portion of the plurality of channels based on the measured ambient power levels on at least one other channel of the plurality of channels, and selecting a channel to transmit on based on the channel assessment values.

In another example, this disclosure is directed to a medical device comprising an antenna and a channel selection module that selects a channel on which to transmit communications via the antenna. The channel selection module obtains measured ambient power levels on a plurality of channels of a frequency band regulation, computes channel assessment values for at least a portion of the plurality of channels based on the measured ambient power levels on at least one other channel of the plurality of channels, and selects a channel to transmit on based on the channel assessment values.

In another example, this disclosure is directed to a medical device comprising means for obtaining measured ambient power levels on a plurality of channels of a frequency band regulation, means for computing channel assessment values for at least a portion of the plurality of channels based on the measured ambient power levels on at least one other channel of the plurality of channels, and means for selecting a channel to transmit on based on the channel assessment values.

This summary is intended to provide an overview of the subject matter described in this disclosure. It is not intended to provide an exclusive or exhaustive explanation of the invention as described in detail within the accompanying drawings and description below. Further details of one or more examples are set forth in the accompanying drawings and the description below. Other features, objects, and advantages will be apparent from the description and drawings, and from the statements provided below.

DETAILED DESCRIPTION

Figure 1:
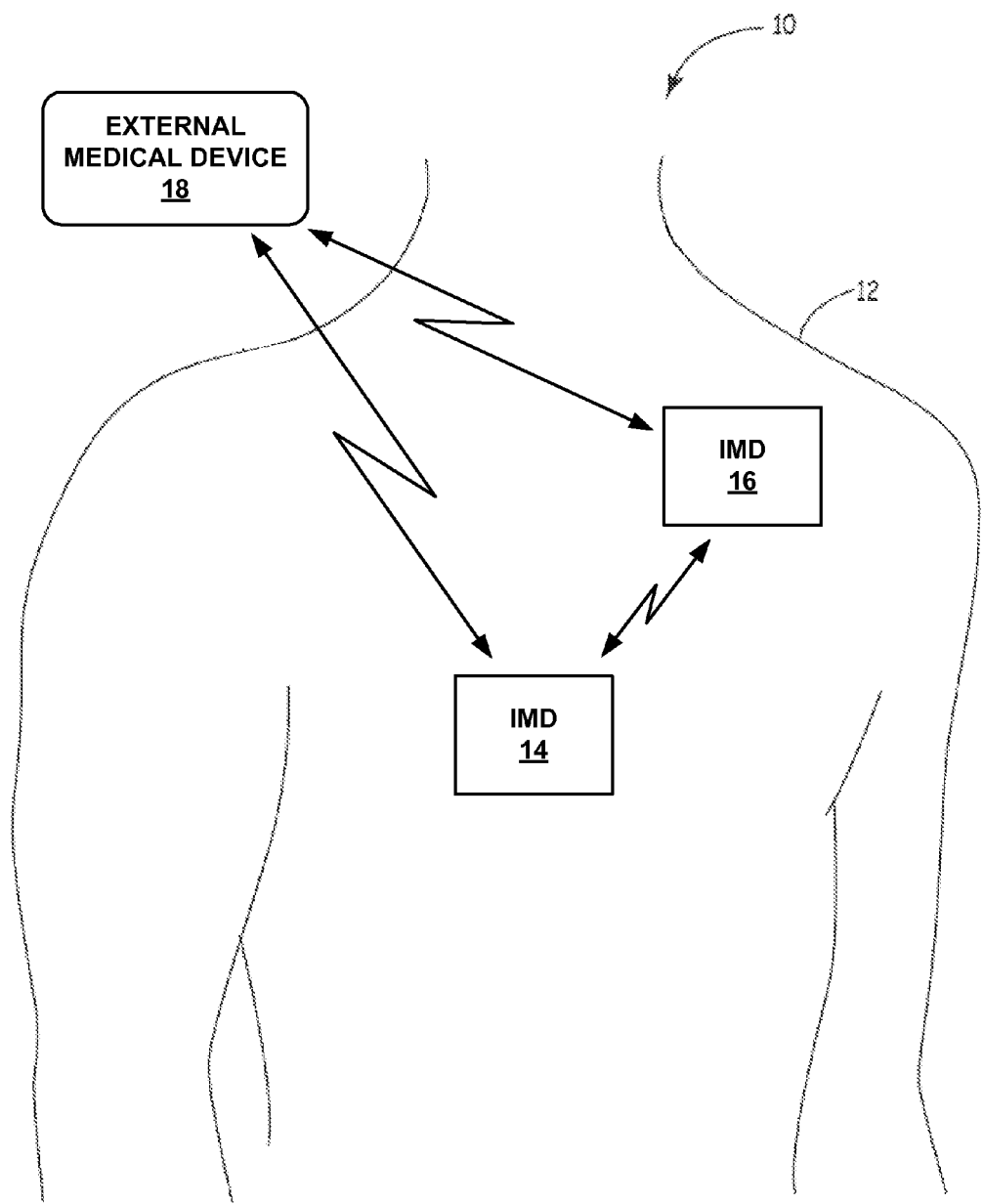
FIG. 1 is a conceptual diagram illustrating an example medical system in which at least one device uses the wireless channel assessment and selection techniques described in this disclosure.

FIG. 1 is a conceptual diagram illustrating an example medical system 10 in which at least one device uses the wireless channel assessment and selection techniques described in this disclosure. The medical devices of medical system 10 may include one or more medical devices that may be used to provide therapy to and/or sense one or more physiological signals of a patient 12. The medical devices of medical system 10 may also include devices that interact with IMDs to program the IMDs and/or retrieve date from the IMDs, such as programming devices and/or monitoring devices. In the example illustrated in FIG. 1, medical system 10 includes an IMD 14, IMD 16, and external medical device 18. Medical system 10 may, however, include more or fewer medical devices that may or may not be implanted within patient 12.

IMD 14 may be any of a variety of medical devices that provide therapy to patient 12, sense physiological or biological conditions of patient 12 or a combination thereof. In some instances, IMD 14 may be a device that provides electrical stimulation therapy in the form of cardiac rhythm management therapy to a heart of patient 12. In such a case, IMD 14 may include one or more implantable leads (not shown) with one or more electrodes that extend from IMD 14 for delivering therapy to and/or sensing physiological signals of a heart of patient 12. The leads may be implanted within one or more atria or ventricles of the heart of patient 12 or a combination thereof. In other words, IMD 14 may be used for single chamber or multi-chamber cardiac rhythm management therapy.

The cardiac rhythm management therapy delivered by IMD 14 may include, for example, pacing, cardioversion, defibrillation and/or cardiac resynchronization therapy (CRT). In other instances, IMD 14 may be a device that provides electrical stimulation to a tissue site of patient 12 proximate a muscle, organ or nerve, such as a tissue proximate a vagus nerve, spinal cord, brain, stomach, pelvic floor or the like to treat various conditions, including movement and affective disorders such as chronic pain, Parkinson's disease, tremor and dystonia, urinary storage and voiding dysfunction, digestion dysfunction, sexual dysfunction or the like.

In other instances, IMD 14 may be a device that delivers a drug or therapeutic agent to patient 12 via an implantable catheter (not shown). IMD 14 may, for example, be implanted within a subcutaneous pocket in an abdomen of patient 12 and the catheter may extend from IMD 14 into the stomach, pelvic floor, brain, intrathecal space of the spine of patient 12 or other location depending on the application. IMD 14 may deliver the drug or therapeutic agent via the catheter to reduce or eliminate the condition of the patient and/or one or more symptoms of the condition of the patient. For example, IMD 14 may deliver morphine or ziconotide to reduce or eliminate pain, baclofen to reduce or eliminate spasticity, chemotherapy to treat cancer, or any other drug or therapeutic agent to treat any other condition and/or symptom of a condition.

Like IMD 14, IMD 16 may also be any of a variety of implantable medical devices that sense a physiological or biological condition of and/or deliver therapy to patient 12. As one example, IMD 16 may be a wireless (or leadless) sensor implanted within patient 12 to sense one or more physiological signals of patient 12. IMD 16 may be implanted at targeted monitoring sites and transmit the sensed signals, thus avoiding limitations associated with lead-based sensors. In some instances, IMD 16 uses the sensed physiological signals to monitor a condition of patient 12 or provide therapy to patient 12 as a function of the sensed physiological signals. Alternatively, or additionally, IMD 16 transmits the sensed physiological signals to another device, such as IMD 14 or external medical device 18, which may in turn monitor the condition of patient 12 or provide therapy to patient 12 as a function of the sensed physiological signals. IMD 16 may sense, sample, and process one or more physiological signals such as heart activity, muscle activity, brain electrical activity, intravascular pressure, blood pressure, blood flow, acceleration, displacement, motion, respiration, or blood/tissue chemistry, such as oxygen saturation, carbon dioxide, pH, protein levels, enzyme levels or other parameter.

Although IMD 16 is described with reference to FIG. 1 as being a wireless sensor, IMD 16 may be any of a variety of other medical devices that deliver therapy, sense physiological signals or both. For example, IMD 16 may be a leadless pacer (sometimes referred to as a wireless pacer). Other examples of medical devices that IMD 16 could be include therapy delivery devices, such as electrical stimulation devices that deliver electrical stimulation to a heart, brain, spinal cord, stomach, pelvic floor or other location within or on patient 12, or drug pumps or infusion pumps that delivers a drug, therapeutic agent, saline solution, or other liquid to locations within patient 12.

External medical device 18 may be a programming device or monitoring device that allows a user, e.g., physician, clinician or technician, to configure a therapy delivered by IMDs 14 and/or 16 or to retrieve data sensed by IMDs 14 and/or 16. External medical device 18 may include a user interface that receives input from the user and/or displays data to the user, thus allowing the user to program the therapy delivered by IMDs 14 and/or 16 or display data retrieved from IMDs 14 and/or 16. External medical device 18 may be a dedicated hardware device with dedicated software for programming or otherwise communicating with IMDs 14 and/or 16. Alternatively, external medical device 18 may be an off-the-shelf computing device running an application that enables external medical device 18 to program or otherwise communicate with IMDs 14 and/or 16. In some examples, external medical device 18 may be a handheld computing device that may be attached to or otherwise carried by patient 12. Alternatively, external medical device 18 may be a computer workstation, such as a CareLink® monitor, available from Medtronic, Inc. of Minneapolis, Minn.

IMD 14, IMD 16 and external medical device 18 may communicate with one another by any of a number of wireless communication techniques. In some instances, IMD 14, IMD 16 and external medical device 18 may be communicatively coupled with each other as well as other medical devices (now shown) to form a local area network, sometimes referred to as a body area network (BAN) or personal area network (PAN). Each device may therefore be enabled to communicate wirelessly along multiple pathways with each of the other networked devices. As such, IMD 14, IMD 16 and external medical device 18 may represent a distributed system of implantable medical devices that cooperate to monitor a condition of and/or provide therapy to patient 12.

Example wireless communication techniques include RF telemetry, but other techniques are also contemplated. In one instance, IMD 14, IMD 16 and/or external medical device 18 may communicate in accordance with the Medical Implant Communications Service (MICS) band regulation. The MICS band regulation defines communication requirements for the 402-405 MHz frequency band. In accordance with the MICS band regulations, the frequency band is divided into ten channels with each channel corresponding to a 300 kilohertz (kHz) sub-band.

The MICS frequency band regulation requires that a device desiring to communicate using the MICS band to perform a clear-channel assessment (CCA), sometimes referred to as listen before talk (LBT) provision. Typically, external medical device 18 performs the CCA process. However, in other instances, one or both of IMD 14 and 16 may be configured to perform the CCA process, particularly in the context of intra-body wireless communication between IMD 14 and IMD 16. The medical device not performing the CCA process may be configured to support a low-power method of sniffing for the presence of an incoming communication signal.

During the CCA, as defined by the MICS frequency band regulation, the device scans all ten of the 300 kHz channels and selects the channel with the lowest ambient power level (the least-noisy or least-interfered with channel) as the channel to transmit on. In other words, the device operating in accordance with the MICS frequency band regulation selects the channel to transmit on based solely on the ambient power levels of each individual channel. Performing CCA increases the likelihood that the device selects an unused MICS channel, thus decreasing the likelihood of interference from multiple communication sessions attempting to use the same MICS channel.

In accordance with the channel assessment and selection techniques described in this disclosure, the device desiring to communicate using the MICS band assesses at least a portion of the channels of the MICS band, and in some instances all of the channels of the MICS band, as a function of the ambient power of the respective channels and the ambient power of at least one other channel. For example, the device may select a subset of the channels of the MICS band that have lowest measured ambient power levels and compute a channel assessment value for each of the selected channels of the subset as a function of the ambient power of immediately adjacent channels, e.g., an immediately prior channel and an immediately subsequent channel. The channel assessment value may, for instance, be a sum of the measured ambient power levels on the adjacent channels, an average measured ambient power level on the adjacent channels, or a ratio between the measured ambient power levels on the respective channel and an average measured ambient power level on the adjacent channels. In other examples, the device may compute the channel assessment value using channels that are not immediately adjacent. In further examples, the device may compute the channel assessment value for at least one of the selected channels as a function of the ambient power on one or more channels located within a different frequency band regulation, e.g., one or more channels in the MEDS band. Thus, the device assesses each channel as a function of the ambient power on at least one other channel instead of or in addition to the ambient power on the individual channels instead of solely as a function of the ambient power on the individual channels.

Assessing and selecting the channels of the frequency band regulation as a function of at least one other channel allows the medical device to better select the channel for use in communicating with other medical devices by accounting for desensitization that may occur due to large RF power usage in adjacent channels. In other words, the CCA process allows multiple simultaneous communication sessions to be collocated with minimal interference. Such a scheme may be particularly useful in an environment in which a number of medical devices are communicating using a limited number of channels, e.g., in a hospital, nursing home, doctor's office, or the like.

Once the external medical device 18 selects the channel to transmit on, external medical device 18 establishes a communication session with one of IMDs 14 or 16 over the selected channel. External programming device and IMD 14 or 16 may establish the communication session using any of a variety of "handshake" mechanisms. External medical device 18 may, for example, transmit wakeup packets followed by open packets on the selected channel. IMD 14 OR 16 may respond to the open packets and, once external medical device 18 receives the open packets back from IMD 14 OR 16, the communication session is established on the selected channel.

Although described in the context of channel assessment and selection using the MICS band regulation, the techniques of this disclosure may be used to assess and select channels using any frequency band regulation. As another example, the techniques may be used to assess and select a channel to transmit on for communication in the Medical External Data Service (MEDS) band regulations. The MEDS frequency band regulation defines a split channel band with a portion of the MEDS band occupying the 401-402 MHz frequency band and a portion of the MEDS band occupying the 405-406 MHz frequency band. The MEDS band is divided into 20 channels with each channel corresponding to a 100 kHz sub-band, with the first ten channels being located in the 401-402 MHz frequency band and the second ten channels being located in the 405-406 MHz frequency band. The MEDS regulation band defines a similar CCA technique to the one described above with respect to the MICS band.

Figure 2:
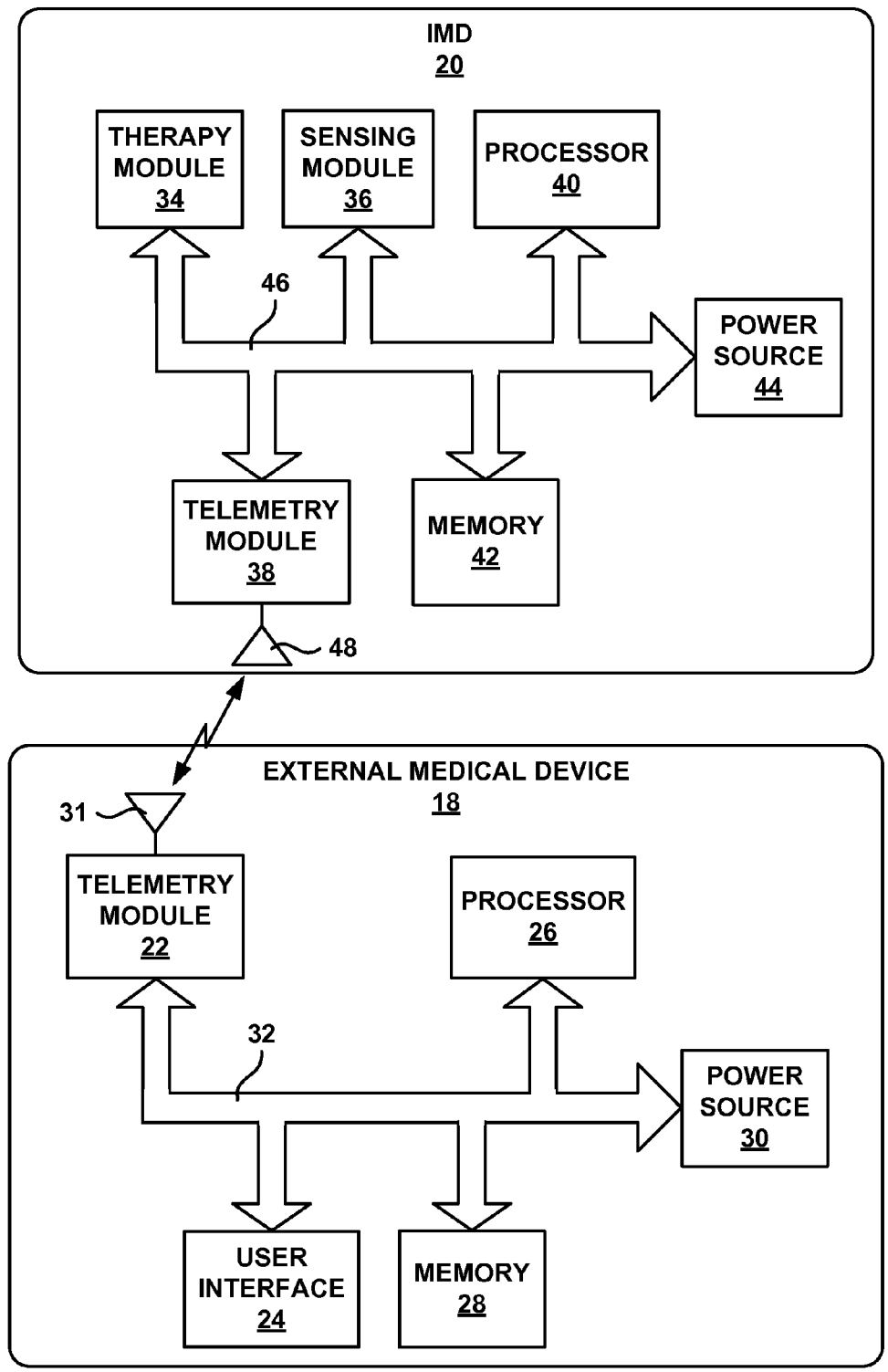
FIG. 2 is a block diagram illustrating components of an example implantable medical device and external medical device.

FIG. 2 is a block diagram illustrating an example IMD 20 and external medical device 18 in further detail. IMD 20 may correspond to IMD 14 or IMD 16 of FIG. 1, or another IMD. External medical device 18 may correspond to a programming device, a monitoring device or other external device located on or in the vicinity of patient 12. As illustrated in the example of FIG. 2, external medical device 18 includes a telemetry module 22, user interface 24, processor 26, memory 28 and power source 30, all of which are interconnected by a data bus 32. IMD 20 includes a therapy module 34, sensing module 36, telemetry module 38, processor 40, memory 42 and power source 44, all of which are interconnected by a data bus 46.

The various components of IMD 20 are coupled to power source 44, which may include a rechargeable or non-rechargeable battery. A non-rechargeable battery may be selected to last for several years, while a rechargeable battery may be charged from an external charging device on a daily or weekly basis. In either case, and especially in the case of the non-rechargeable battery, the amount of power of the battery is limited.

IMD 20 may sense one or more physiological signals or conditions of patient 12. In some instances, IMD 20 may not provide therapy to patient 12, but only provides monitoring of patient 12 as in the case of an implantable loop recorder. In such cases, IMD 20 may not include therapy module 34. Sensing module 36 is configured to monitor one or more physiological signals using one or more sensors connected to sensing module 36. In one example, sensing module 36 is configured to monitor signals sensed by one or more of electrodes on leads extending from IMD 20. In another example, sensing module 36 may be configured to monitor signals sensed by a lead within or on IMD 20. In a further example, sensing module 36 may be configured to receive signals sensed by one or more wireless or lead-less sensors and transmitted wirelessly to IMD 20. The one or more sensors may sense physiological signals such as heart activity (e.g., electrocardiogram (ECG) signals), muscle activity (e.g., electromyography (EMG) signals), brain electrical activity (e.g., electroencephalography (EEG) signals), heart rate, intravascular pressure, blood pressure, blood flow, acceleration, displacement, motion, respiration, or blood/tissue chemistry such as oxygen saturation, carbon dioxide, pH, protein levels, enzyme levels or other parameter.

Sensing module 36 may store the sensed signals in memory 42. In some instances, sensing module 36 may store the sensed signals in raw form. In other instances, sensing module 36 may process the sensed signals and store the processed signals in memory 42. For example, sensing module 36 may amplify and filter the sensed signal and store the filtered signal in memory 42. The signals stored by sensing module 36 may, in some cases, be retrieved and further processed by processor 40.

IMD 20 may also provide therapy, such as electrical stimulation therapy or drug delivery therapy, to patient 12 in accordance with parameters of one or more selected therapy programs. In particular, processor 36 controls therapy module 34 to deliver therapy to patient 12 according to one or more therapy programs, which may be received from external medical device 18 and stored in memory 42. In the case of electrical stimulation therapy, therapy module 34 may include a stimulation generator that generates and delivers electrical stimulation therapy, e.g., in the form of pulses or shocks. Processor 40 may control the stimulation generator to deliver electrical stimulation pulses with amplitudes, pulse widths, frequency, and/or electrode polarities specified by the one or more therapy programs. In the case of drug delivery therapy, therapy module 34 may include a pump that delivers a drug or therapeutic agent to patient 12. Processor 40 may control the pump to deliver the drug or therapeutic agent with the dosage and frequency (or rate) specified by the one or more therapy programs.

Processor 40 may include any one or more of a microprocessor, a controller, a DSP, an ASIC, a FPGA, or equivalent discrete or integrated logic circuitry. In some examples, processor 40 may include multiple components, such as any combination of one or more microprocessors, one or more controllers, one or more DSPs, one or more ASICs, or one or more FPGAs, as well as other discrete or integrated logic circuitry. The functions attributed to processor 40 herein may be embodied as software, firmware, hardware or any combination thereof.

Memory 42 includes computer-readable instructions that, when executed by processor 40, cause IMD 20 and processor 40 to perform various functions attributed to IMD 20 and processor 40 herein. Memory 42 may include any volatile, non-volatile, magnetic, optical, or electrical media, such as a RAM, ROM, NVRAM, EEPROM, flash memory, MRAM, or any other digital media.

Processor 40 controls telemetry module 38 to transmit communications to and/or receive communications from another medical device, such as external medical device 18. Telemetry module 38 may also transmit communications to and/or receive communications from other external and/or implanted medical devices. Processor 40 may provide the data to be transmitted to external medical device 18 and the control signals for telemetry circuitry within telemetry module 38, e.g., via data bus 46. Telemetry module 38 transmits the data to external medical device 18 in accordance with the control signals from processor 40. Telemetry module 38 may provide data received from external medical device 18 to processor 40. Processor 40 may analyze the received data, store the received data within memory 42 and configure components of IMD 20 in accordance with the received data.

Telemetry module 38 includes any suitable hardware, firmware, software or any combination thereof for communicating with another device, such as external medical device 18. For example, telemetry module 38 may include appropriate modulation, demodulation, frequency conversion, filtering, and amplifier components for transmission and reception of data, including radio frequency (RF) components and antenna 48, as applicable.

A user may interact with external medical device 18 to program IMD 20 to provide therapy in accordance with a selected therapy program and/or view data retrieved from IMD 20. The user may, for example, interact with external medical device 18 via user interface 24 to select therapy programs (e.g., sets of stimulation parameters), generate new therapy programs and/or modify therapy programs through individual or global adjustments. User interface 24 may include, for example, a keypad and a display, which may be, for example, a cathode ray tube (CRT) display, a liquid crystal display (LCD) or light emitting diode (LED) display. The keypad may take the form of an alphanumeric keypad or a reduced set of keys associated with particular functions. External medical device 18 can additionally or alternatively include a peripheral pointing device, such as a mouse, via which a user may interact with the user interface. In some embodiments, the display of external medical device 18 may include a touch screen display, and a user may interact with external medical device 18 via the display.

Processor 26 controls telemetry module 22 to transmit the parameters of the one or more selected therapy programs, which may be stored within memory 28 or directly input by the user via user interface 24, to telemetry module 38 of IMD 20. Telemetry module 22, under the control of processor 26, may also receive data from telemetry module 38 of IMD 20, which may include sensed physiological parameters, diagnosis generated based on the sensed physiological parameters, a log of delivered therapies, information regarding the amount of remaining battery power or the like. Processor 26 may store the retrieved data in memory 28 for later processing or transmission to another device, e.g., a remote server.

Telemetry module 22 communicates wirelessly with IMD 20 and, more specifically, with telemetry module 38 of IMD 20. Telemetry module 22, like telemetry module 38 of IMD 20, may include any suitable hardware, firmware, software or any combination thereof for communicating with IMD 20. For example, telemetry module 22 may include appropriate modulation, demodulation, frequency conversion, filtering, and amplifier components for transmission and reception of data, including radio frequency (RF) components and antenna 31, as applicable. In some instances, telemetry module 22 may include two or more sets of RF components, e.g., one for communication with IMD 20 and one for communication with another computing device (e.g., remote server).

As described above, IMD 20 and external medical device 18 may communicate with one another using any of a variety of RF frequency band regulations, including MICS band regulation or MEDS band regulation. The frequency band regulations may require that external medical device 18 or IMD 20 perform a channel assessment to select a channel over which to establish the communication session. Although described below in the context of the MICS band regulation, the channel assessment techniques may be used in the context of other frequency band regulations, including the MEDS band regulation. Furthermore, although the channel assessment techniques are described as being performed by telemetry module 22 of external medical device 18, the channel assessment may, in other instances, be performed by telemetry module 38 of IMD 20.

Telemetry module 22, or a channel selection module (not shown) of telemetry module 22, assesses at least a portion of the channels of the MICS band as a function of the ambient power on the respective channels and the ambient power on at least one other channel of the MICS band. In one instance, telemetry module 22 may measure ambient power on each of the channels of the MICS band. Telemetry module 22 may, for example, measure a received signal strength indication (RSSI) for each of the channels. Telemetry module 22 may select two or more of the channels with a lowest measured ambient power. Telemetry module 22 may compute a channel assessment value for the two or more selected channels as a function of ambient power on the at least one other channel. For example, telemetry module 22 may compute a sum of the measured ambient power levels on the immediately adjacent channels, i.e., the channel immediately prior (in frequency) to the selected channel and the channel immediately subsequent (in frequency) to the selected channel. As another example, telemetry module 22 may compute an average measured ambient power level on the immediately adjacent channels. As a further example, telemetry module 22 may select the largest ambient power of the adjacent channels as the channel assessment value.

As another example, telemetry module 22 may compute power ratios for the selected channels. The power ratio of each channel may be computed as the ratio between the ambient power measured on the respective channels and the average ambient power. In this manner, telemetry module 22 accounts for the ambient power on the selected channels as well as the ambient power on at least one other channel. Other channel assessment metrics may be computed, however, to account for the ambient power on the selected channel.

Telemetry module 22 selects the channel to transmit on based on the channel assessment values of the selected channels. For example, telemetry module 22 may select the channel with the smallest sum or average of the measured ambient power levels on the immediately adjacent channels as the channel for use in transmitting. As another example, telemetry module 22 may select the channel with the largest power ratio as the channel for use in transmitting. In some cases, the channel selected based on the channel assessment value is not the channel with the smallest ambient power. In other words, the channel selected using the techniques of this disclosure may be different than the channel that would be selected using the CCA techniques specified in the MICS band regulation. Instead, the channel selected in accordance with the techniques of this disclosure provides better telemetry performance even though it may not have the lowest on-channel ambient power. This is because the channel assessment and selection techniques account for desensitization that may be experienced due to large RF power in adjacent channels.

In other instances, telemetry module 22 assesses all of the channels of the MICS band as a function of ambient power on at least one other channel of the MICS band. For example, telemetry module 22 may measure ambient power on each of the channels and compute channel assessment values for each of the channels as a function of the ambient power on the respective channels and the ambient power on at least one other channel. As described above, telemetry module 22 may compute a power ratio for each channel of the MICS band. Telemetry module 22 may then select the channel corresponding to the largest power ratio as the channel over which to transmit.

Although in the examples described above, telemetry module 22 computes the channel assessment value based on the ambient power measured on the immediately adjacent channels of the MICS band, telemetry module 22 may compute the ratio as a function of more or fewer channels. For example, telemetry module 22 may compute the channel assessment value as a function of only one immediately adjacent channel. As another example, telemetry module 22 may compute the channel assessment value as a function of more than the two immediately adjacent channels. Telemetry module 22 may, for instance, compute a weighted sum of the ambient power measurements on four adjacent channels, e.g., two previous adjacent channels and two subsequent adjacent channels. In another example, telemetry module 22 may compute a weighted sum of the ambient power measurements on all channels of the MICS band. The channels located closer to the selected channel may be provided with larger weights than the channels located further from the selected channel. The weights assigned to the channels may decrease linearly or non-linearly as a function of the distance (in frequency) from the respective channels.

Moreover, telemetry module 22 may compute the channel assessment value of the at least a portion of the channels as a function of ambient power measurements of at least one channel of a different frequency band regulation than the frequency band regulation of the selected channel. For example, telemetry module 22 may compute the channel assessment value for a first channel of the MICS band regulation as a function of the ambient power on the first channel, the ambient power on the second channel of the MICS band regulation and ambient power measured on one or more channels of the MEDS band regulation. Telemetry module 22 may compute the channel assessment value of the first channel of the MICS band regulation as a function of the channels 8-10 of the MEDS band regulation (i.e., the last three channels in the 401-402 MHz portion of the split-band). The reason external device 18 may look at three channels is because the size of each of the MEDS band channels is 100 kHz whereas the size of the channel of the MICS band is 300 kHz. Thus, analyzing the three channels looks at a frequency range in the MEDS band equivalent in size to the channels of the channels in the MICS band. Telemetry module 22 may, however, analyze more or fewer channels in the other frequency band regulation.

Assessing and selecting the channels of the frequency band regulation as a function of at least one other channel allows the telemetry module of the medical device to better select the channel for use in communicating with other medical devices by accounting for desensitization that may occur due to large RF power usage in adjacent channels in the same frequency band or in channels of other frequency band regulations. Such a scheme may be particularly useful in an environment in which a number of medical devices are communicating using a limited number of channels, e.g., in a hospital, nursing home, doctor's office, or the like.

Although the techniques of this disclosure are described as being performed by telemetry module 22 of external medical device 18, other components of external medical device 18 may perform the channel assessment and selection. For example, processor 26 may include a channel selection module that obtains the measured ambient power levels and selects the channel to transmit on in accordance with the channel assessment and selection techniques described above. Moreover, telemetry module 38, processor 40 or other component of IMD 20 may include a channel selection module to perform the channel assessment and selection techniques in addition to or instead of the components of external medical device 18. This may be the case in which two or more implanted medical devices, e.g., IMD 14 and 16 of FIG. 1, communicate using intra-body wireless communication.

Processor 26 may include one or more of a microprocessor, a controller, a digital signal processor (DSP), an application specific integrated circuit (ASIC), a field-programmable gate array (FPGA), or equivalent discrete or integrated logic circuitry. In some examples, processor 26 may include multiple components, such as any combination of one or more microprocessors, one or more controllers, one or more DSPs, one or more ASICs, or one or more FPGAs, as well as other discrete or integrated logic circuitry. The functions attributed to processor 26 herein may be embodied as software, firmware, hardware or any combination thereof.

Memory 28 includes computer-readable instructions that, when executed by processor 26, cause external medical device 18 and processor 26 to perform various functions attributed to external medical device 18 and processor 26 herein. Memory 28 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, magnetoresistive random access memory (MRAM), or any other digital media.

Power source 30 of external medical device 18 delivers operating power to the components of external medical device 18. Power source 30 may include a battery and a power generation circuit to produce the operating power for the components of external medical device 18. In some examples, the battery may be rechargeable (e.g., nickel cadmium or lithium ion batteries) to allow extended operation. Recharging may be accomplished by electrically coupling power source 30 to a cradle or plug that is connected to an alternating current (AC) outlet. In addition or alternatively, recharging may be accomplished through proximal inductive interaction between an external charger and an inductive charging coil within external medical device 18. In other embodiments, non-rechargeable batteries (e.g., non-rechargeable lithium based batteries such as lithium iodide) may be used. In addition, external medical device 18 may be directly coupled to an AC outlet to power external medical device 18.

Figure 3:
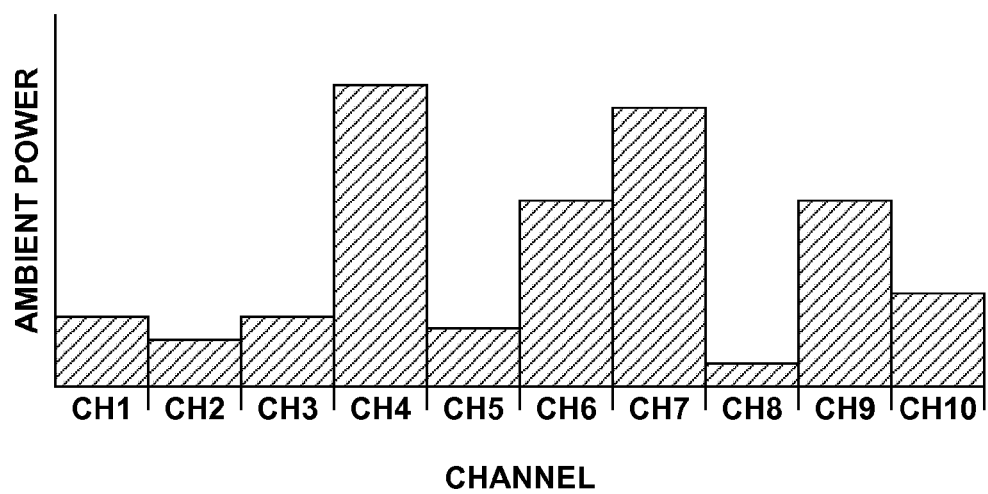
FIG. 3 is a bar graph illustrating example ambient power measurements for channels of a frequency band regulation.

FIG. 3 is a bar graph illustrating example ambient power measurements for channels of a frequency band regulation. For purposes of description, the channels will be described in the context of the channels of the MICS band regulation, i.e., ten 300 kilohertz (kHz) channels in the 402-405 MHz frequency band. However, the techniques of this disclosure are applicable to other frequency band regulations, including the MEDS band regulation. Each of the bars represents a measured ambient power on the respective channel.

As described above, the medical device desiring to transmit using the MICS band, e.g., external medical device 18, assesses at least a portion of the channels of the MICS band as a function of the ambient power measured on the respective channel and the ambient power measured on at least one other channel. Telemetry module 22 of external medical device 18 may select a subset of the channels having the lowest measured ambient power levels and assess the subset of channels as a function of the ambient power measured on at least one other channel. For example, telemetry module 22 may select the three channels with the lowest ambient power measurements, e.g., channel 2 (CH2), channel 5 (CH5) and channel 8 (CH8) in the example illustrated in FIG. 3. In other examples, telemetry module 22 may assesses all of the channels of the MICS band as a function of the ambient power measured on the respective channel and the ambient power measured on at least one other channel.

Telemetry module 22 computes a channel assessment value for channel 2, channel 5 and channel 8. In some instances, telemetry module 22 may compute the channel assessment value for channel 2, channel 5 and channel 8 based on immediately adjacent channels, i.e., the channel immediately prior (in frequency) to the selected channel and the channel immediately subsequent (in frequency) to the selected channel. For example, telemetry module 22 may compute a sum of the measured ambient power levels on the immediately adjacent channels. As another example, telemetry module 22 may compute an average measured ambient power level on the immediately adjacent channels. In a further example, telemetry module 22 may compute the power ratio for each of the selected channels as the ratio between the power measured on the respective channel and the average power measured on the immediately adjacent channels.

In the example illustrated in FIG. 3, channel 1 and channel 3 are the immediately adjacent channels of channel 2, channel 4 and channel 6 are the immediately adjacent channels of channel 5, and channel 7 and channel 9 are the immediately adjacent channels of channel 8. In instances in which channel 1 or channel 10 are selected as part of the subset of channels with the lowest ambient power measurement, the channel assessment value may be computed as a function of ambient power measurements of one or more channels in an adjacent frequency band regulation (e.g., MEDS band regulation) as described in detail above.

Telemetry module 22 selects the channel that has the channel assessment value indicative of a best estimated telemetry performance. For example, telemetry module 22 may select the channel with the smallest power level sum of immediately adjacent channels as the channel over which to transmit. As another example, telemetry module 22 may select the channel with the largest power ratio as the channel over which to transmit. In the example illustrated in FIG. 3, telemetry module 22 would select channel 2 for transmission. Thus, although channel 2 is not the channel with the lowest ambient power, channel 2 is selected because it is more likely to result in better telemetry performance. Conventional CCA, as defined by the MICS band regulation, would select channel 8 since channel 8 has the lowest on-channel ambient power. However, selecting channel 8 in accordance with convention CCA techniques fails to account for desensitization of the receiver of telemetry module 22 due to large amounts of ambient power on adjacent channels. As such, channel 2 may actually provide better telemetry performance.

Figure 4:
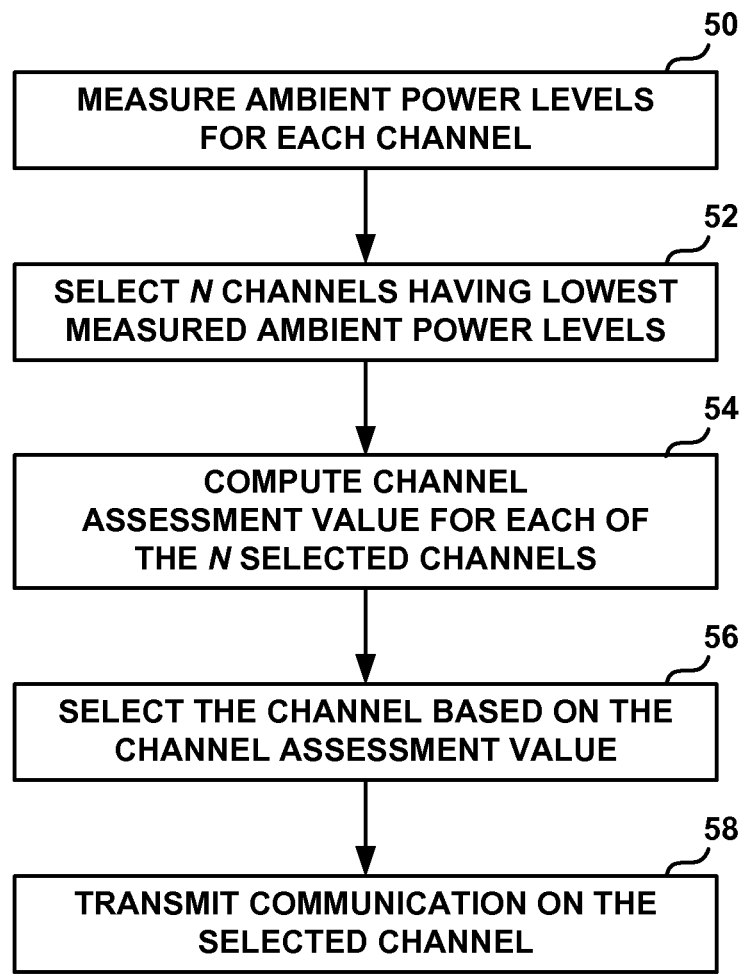
FIG. 4 is a flow diagram illustrating an example operation of a telemetry module of a medical device performing the channel assessment and selection techniques of this disclosure.

FIG. 4 is a flow diagram illustrating an example operation of a telemetry module of a medical device performing the channel assessment and selection techniques of this disclosure. FIG. 4 is described with respect to telemetry module 22 of external medical device 18. However, other component of external medical device 18 and/or telemetry module 38 or other components of IMD 20 may perform the channel assessment and selection techniques of this disclosure. Telemetry module 22 measures ambient power levels on each of the channels of the MICS band (50). Telemetry module 22 selects N of the channels having a lowest measured ambient power level (52). In one example, N may be equal to 3.

Telemetry module 22 computes a channel assessment value for each of the N selected channels as a function of ambient power level on at least one other channel (54). For example, telemetry module 22 may compute the channel assessment values as a sum of the measured ambient power levels on the immediately adjacent channels. As another example, telemetry module 22 may compute the channel assessment values as an average measured ambient power level on the immediately adjacent channels. In a further example, telemetry module 22 may compute the channel assessment values as a ratio between the power measured on the respective channel and the average power measured on the immediately adjacent channels. Telemetry module 22 may compute the channel assessment values as a function of more than the two immediately adjacent channels, e.g., as a function of a weighted sum of the ambient power measurements of more than two channels. In some instances, telemetry module 22 may even account for ambient power on one or more channels of a different frequency band regulation than the frequency band regulation of the selected channels.

Telemetry module 22 selects one of the N selected channels as the channel for transmitting on based on the channel assessment values (56). For example, telemetry module 22 may select the channel with the smallest sum of power levels of immediately adjacent channels as the channel over which to transmit. As another example, telemetry module 22 may select the channel with the largest power ratio as the channel over which to transmit. In this manner, telemetry module 22 selects the channel that has the channel assessment value indicative of a best estimated telemetry performance.

Telemetry module 22 establishes a communication session with the other medical device, e.g., IMD 20, over the selected channel (58). Assessing and selecting the channels of the frequency band regulation as a function of at least one other channel allows the medical device to better select the channel for use in communicating with other medical devices by accounting for desensitization that may occur due to large RF power usage in adjacent channels.

Figure 5:
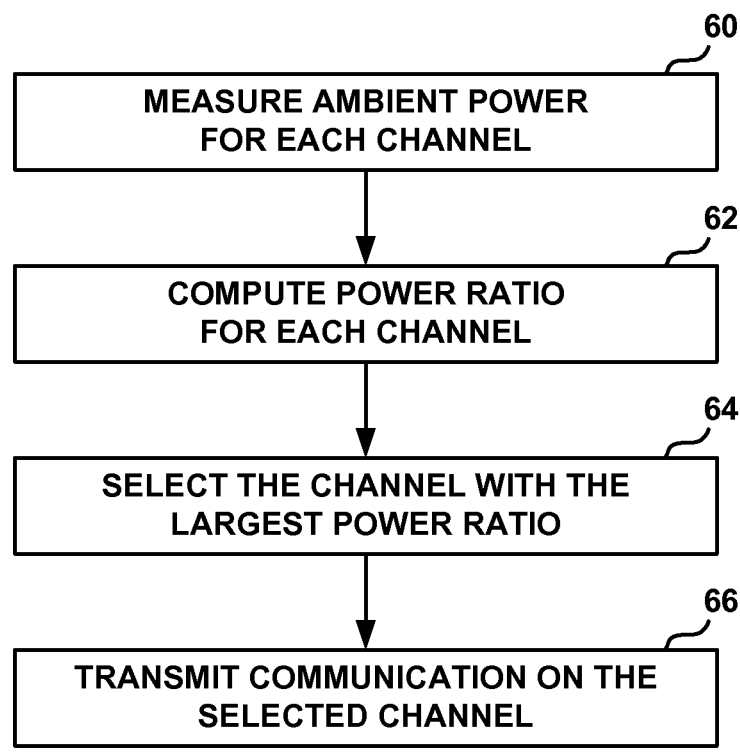
FIG. 5 is a flow diagram illustrating another example operation of a telemetry module of a medical device performing the channel assessment and selection techniques of this disclosure.

FIG. 5 is a flow diagram illustrating an example operation of a telemetry module of a medical device performing the channel assessment and selection techniques of this disclosure. FIG. 5 is described with respect to telemetry module 22 of external medical device 18. However, telemetry module 38 of IMD 20 may perform the channel assessment and selection techniques of this disclosure. Telemetry module 22 measures ambient power levels on each of the channels of the MICS band (60).

Telemetry module 22 computes a channel assessment value, e.g., power ratio, for each channel of the MICS band as a function of ambient power level on at least one other channel (62). Telemetry module 22 selects the channel with the largest power ratio as the channel for transmitting on (64). Telemetry module 22 establishes a communication session with the other medical device, e.g., IMD 20, over the selected channel (66).

The techniques described in this disclosure may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, or other devices. The term "processor" or "processing circuitry" may generally refer to any of the foregoing circuitry, alone or in combination with other circuitry, or any other equivalent circuitry.

Such hardware, software, or firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

Various examples have been described. These and other examples are within the scope of the following claims.

The invention claimed is:

1. A medical device comprising:
   an antenna; and
   a channel selection module that selects a channel on which to transmit communications via the antenna, wherein the channel selection module:
   obtains measured ambient power levels on a plurality of channels of a frequency band regulation,
   based on the measured ambient power levels of the plurality of channels, selects a subset of N channels from the plurality of channels that have the N lowest measured ambient power levels, wherein the subset of channels comprises less than all of the plurality of channels,
   for each respective channel in the subset of channels, mathematically computes a channel assessment value as a function of the measured ambient power level of at least one channel of the plurality of channels other than the respective channel in the subset of channels for which the channel assessment value is being computed, and selects a channel from the subset of channels to transmit on based on at least the computed channel assessment values.

2. The device of claim 1, wherein the channel selection module mathematically computes the channel assessment value for each respective channel in the subset of the channels by one of computing a sum of the measured ambient power levels of the at least one channel of the plurality of channels other than the respective channel for which the channel assessment value is being computed and computing an average measured ambient power level on the at least one channel of the plurality of channels other than the respective channel for which the channel assessment value is being computed.

3. The device of claim 2, wherein the channel selection module selects a channel of the subset of channels that has a lowest channel assessment value.

4. The device of claim 1, wherein the channel selection module mathematically computes each channel assessment value based on the measured ambient power level of the respective channel and at least a first other channel immediately adjacent, in frequency, to the respective channel and a second other channel not immediately adjacent, in frequency, to the respective channel, and associates weights with each of the at least one other channel, each of the weights decreasing as a function of distance, in frequency, from the respective channel, multiplies the measured ambient power levels of the at least one other channel by the associated weights, and uses the weighted ambient power levels of the at least one other channel to obtain the channel assessment value of the respective channel.

5. The device of claim 1, wherein the channel selection module mathematically computes each channel assessment value by computing a ratio between the measured ambient power level on the respective channel for which the channel assessment value is being computed and an average measured ambient power level on the at least one channel of the plurality of channels other than the respective channel for which the channel assessment value is being computed.

6. The device of claim 5, wherein the channel selection module selects the channel to transmit on as the channel having a largest computed ratio and transmits at least one communication on the selected channel.

7. The device of claim 1, wherein the channel selection module mathematically computes the channel assessment values based on the measured ambient power levels of a first other channel immediately adjacent, in frequency, to the respective channel and a second other channel immediately adjacent, in frequency, to the respective channel.

8. The device of claim 7, wherein at least one of the first other channel and the second other channel belongs to a different frequency band regulation than the frequency band regulation of the respective channel.

9. The device of claim 1, wherein the frequency band regulation comprises one of the Medical Implant Communications Service (MICS) band regulation and the Medical External Data Service (MEDS) band regulations.

10. The device of claim 1, wherein the medical device includes one of an implantable medical device, an external programming device, or an external monitoring device.

11. A medical device comprising:
means for obtaining measured ambient power levels on a plurality of channels of a frequency band regulation;
based on the measured ambient power levels of the plurality of channels, means for selecting a subset of N channels from the plurality of channels that have the N lowest measured ambient power levels, wherein the subset of channels comprises less than all of the plurality of channels;
means for mathematically computing for each respective channel in the subset of channels a channel assessment value as a function of the measured ambient power level of at least one channel of the plurality of channels other than the respective channel in the subset of channels for which the channel assessment value is being computed; and
means for selecting a channel from the subset of channels to transmit on based on the computed channel assessment values.

12. The device of claim 11, wherein
the means for mathematically computing the channel assessment value for each channel of the subset computes one of a sum of the measured ambient power levels of the at least one channel of the plurality of channels other than the respective channel for which the channel assessment value is being computed and an average measured ambient power level on the at least one channel of the plurality of channels other than the respective channel for which the channel assessment value is being computed, and
the means for selecting the channel to transmit on selects a channel of the subset of channels that has a lowest one of the sum of the measured ambient power levels and the average of the measured ambient power levels.

13. The device of claim 11, wherein
the means for mathematically computing the channel assessment value for each channel of the subset computes each channel assessment value by computing a ratio between the measured ambient power level on the respective channel for which the channel assessment value is being computed and an average measured ambient power level on the at least one channel of the plurality of channels other than the respective channel for which the channel assessment value is being computed;
the means for selecting the channel to transmit on selects the channel having the largest ratio,
the device further comprising means for transmitting at least one communication on the selected channel.

14. The device of claim 11, wherein the means for mathematically computing channel assessment values computes each channel assessment value based on measured ambient power level on the respective channel and the measured ambient power levels of a first other channel immediately adjacent, in frequency, to the respective channel and a second other channel immediately adjacent, in frequency, to the respective channel, and at least one of the first other channel and the second other channel belongs to a different frequency band regulation than the frequency band regulation of the respective channels.

15. The device of claim 11, wherein the means for mathematically computing channel assessment values computes each channel assessment value based on the measured ambient power level of the respective channel and at least a first other channel immediately adjacent, in frequency, to the respective channel and a second other channel not immediately adjacent, in frequency, to the respective channel, and associates weights with each of the at least one other channel, each of the weights decreasing as a function of distance, in frequency, from the respective channel, multiplies the measured ambient power levels of the at least one other channel by the associated weights, and uses the weighted ambient power levels of the at least one other channel to obtain the channel assessment value of the respective channel.

16. A medical device comprising:

an antenna; and a channel selection module that selects a channel on which to transmit communications via the antenna, wherein the channel selection module obtains measured ambient power levels on a plurality of channels of a frequency band regulation, computes a channel assessment value for each of at least a portion of the plurality of channels, and selects the channel to transmit on from the at least a portion of the plurality of channels based on the computed channel assessment values, wherein the channel selection module computes each channel assessment value based on the measured ambient power level of a respective channel for which the channel assessment value is being computed and at least a first other channel immediately adjacent, in frequency, to the respective channel and a second other channel not immediately adjacent, in frequency, to the respective channel, associates weights with each of the at least first and second other channel, each of the weights associated with each of the channels decreases as a function of distance, in frequency, from the respective channel, multiplies the measured ambient power levels of the at least one other channel by the associated weights, and uses the weighted ambient power levels of the at least one other channel to obtain the channel assessment value of the respective channel.

* * * * *